(12) United States Patent
Lafontaine et al.

(10) Patent No.: US 6,808,531 B2
(45) Date of Patent: Oct. 26, 2004

(54) IN-STENT ABLATIVE TOOL

(75) Inventors: Daniel M. Lafontaine, Plymouth, MN (US); Kurt M. Laundroche, Snohomish, WA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 10/306,997

(22) Filed: Nov. 26, 2002

(65) Prior Publication Data
US 2003/0078606 A1 Apr. 24, 2003

Related U.S. Application Data

(63) Continuation of application No. 09/836,957, filed on Apr. 17, 2001, now Pat. No. 6,500,186.

(51) Int. Cl.$^7$ .............................................. A61B 17/22
(52) U.S. Cl. ........................ 606/159; 606/167; 606/180
(58) Field of Search ................................ 606/159, 167, 606/180, 168, 170; 623/1.12

(56) References Cited

U.S. PATENT DOCUMENTS

| | | | |
|---|---|---|---|
| 4,030,503 A | | 6/1977 | Clark, III |
| 5,100,425 A | | 3/1992 | Fischell et al. |
| 5,209,749 A | * | 5/1993 | Buelna ...................... 606/159 |
| 5,224,945 A | | 7/1993 | Pannek |
| 5,226,909 A | | 7/1993 | Evans et al. |
| 5,312,427 A | | 5/1994 | Shturman |
| 5,314,438 A | | 5/1994 | Shturman |
| 5,320,634 A | | 6/1994 | Vigil et al. |
| 5,356,418 A | | 10/1994 | Shturman |
| 5,395,311 A | * | 3/1995 | Andrews ..................... 606/159 |
| 5,443,443 A | | 8/1995 | Shiber |
| 5,616,149 A | * | 4/1997 | Barath ........................ 606/159 |
| 5,622,188 A | | 4/1997 | Plaia et al. |
| 5,628,746 A | * | 5/1997 | Clayman ..................... 606/159 |
| 5,632,755 A | | 5/1997 | Nordgren et al. |
| 5,728,129 A | * | 3/1998 | Summers ..................... 606/159 |
| 5,836,868 A | | 11/1998 | Ressemann et al. |
| 5,842,479 A | | 12/1998 | Plaia et al. |
| 5,843,103 A | | 12/1998 | Wulfman |
| 5,882,329 A | | 3/1999 | Patterson et al. |
| 5,897,567 A | | 4/1999 | Ressemann et al. |
| 5,902,263 A | * | 5/1999 | Patterson et al. ........... 606/159 |
| 5,941,869 A | | 8/1999 | Patterson et al. |
| 6,015,420 A | * | 1/2000 | Wulfman et al. ........... 606/168 |
| 6,146,395 A | | 11/2000 | Kanz et al. |
| 6,156,046 A | | 12/2000 | Passafaro et al. |
| 6,183,487 B1 | | 2/2001 | Barry et al. |
| 6,270,509 B1 | * | 8/2001 | Barry et al. ................. 606/159 |
| 6,306,151 B1 | | 10/2001 | Lary |
| 6,319,242 B1 | | 11/2001 | Patterson et al. |
| 6,328,750 B1 | * | 12/2001 | Berry et al. ................. 606/168 |
| 6,482,216 B1 | * | 11/2002 | Hiblar et al. ................ 606/159 |
| 6,500,186 B2 | * | 12/2002 | Lafontaine et al. ......... 606/159 |
| 6,652,548 B2 | * | 11/2003 | Evans et al. ................. 606/159 |
| 2002/0016624 A1 | * | 2/2002 | Patterson et al. ........... 606/168 |

FOREIGN PATENT DOCUMENTS

| | | |
|---|---|---|
| EP | 0 533 511 A1 | 3/1993 |
| WO | WO 99/23958 A1 | 5/1999 |

* cited by examiner

Primary Examiner—Roy D Gibson
Assistant Examiner—Henry M Johnson, III
(74) Attorney, Agent, or Firm—Christensen O'Connor Johnson Kindness PLLC

(57) ABSTRACT

A system for removing matter from a partially or totally occluded stent includes a cutter that is urged radially outward toward the inner surface of the stent. Preferably, the cutter has a hardness that is less than or equal to the hardness of the material used to make the stent. Aspiration may be provided to remove portions of the occluding material from the vessel.

5 Claims, 6 Drawing Sheets

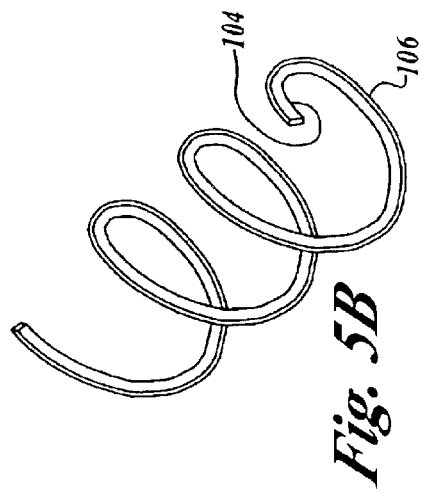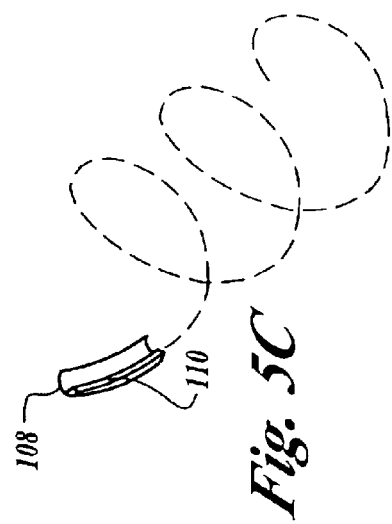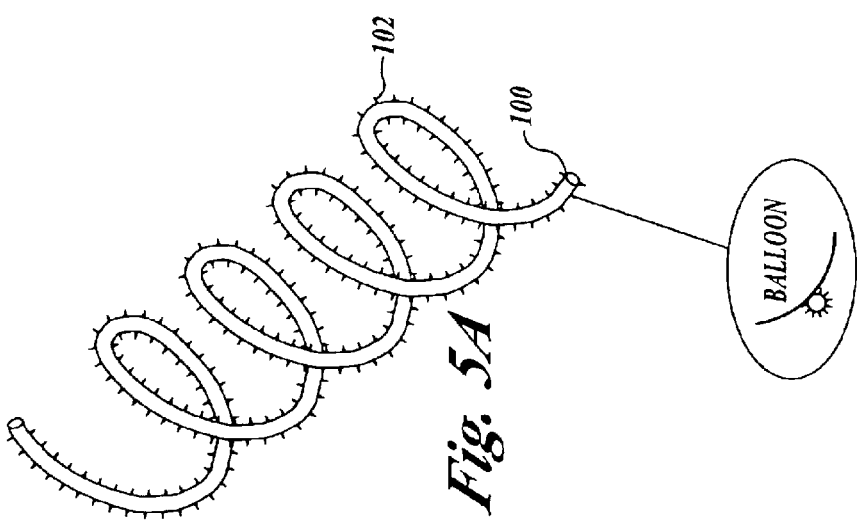

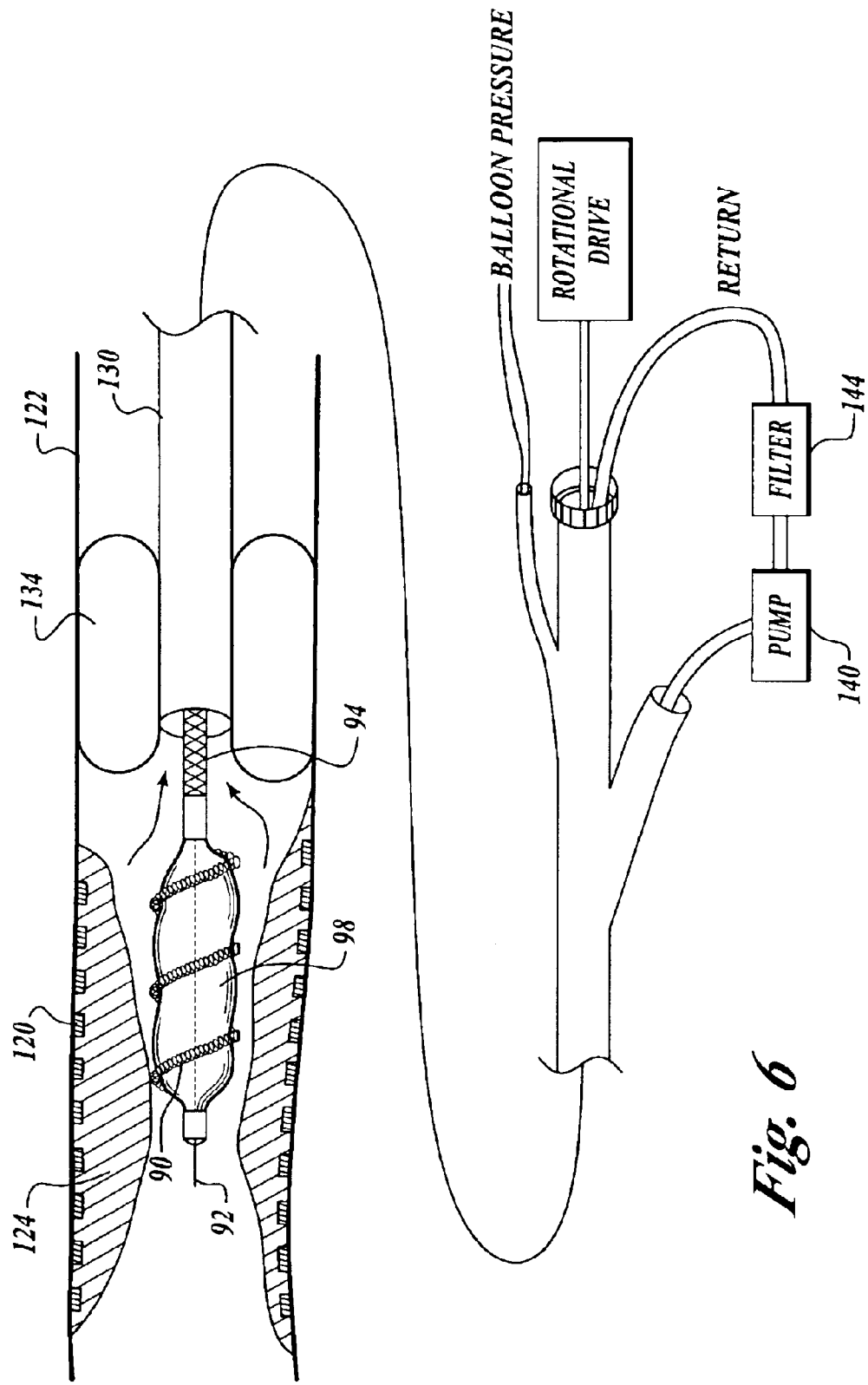

IN-STENT ABLATIVE TOOL

CROSS-REFERENCE TO RELATED APPLICATION

This application is a continuation of application Ser. No. 09/836,957, filed Apr. 17, 2001, now U.S. Pat No. 6,500,186, priority from the filing date of which is hereby claimed under 35 U.S.C. §120.

FIELD OF THE INVENTION

The present invention relates to medical devices in general, and in particular, to rotational atherectomy devices.

BACKGROUND OF THE INVENTION

One of the most common types of vascular diseases afflicting Americans today involves the narrowing of blood vessels by plaque or other materials. Left untreated, such narrowed vessels can contribute to high blood pressure, strokes, or cardiac arrest.

One of the most common techniques for treating a fully or partially blocked vessel is to bypass the blockage with a healthy vessel obtained from elsewhere in the body. A less traumatic approach involves the insertion of a balloon angioplasty device into the vessel and expanding the balloon to compress the occlusion against the vessel wall. Another minimally invasive technique is an atherectomy procedure, where a high-speed cutting device such as the Rotoblator™, produced by SCIMED Life Systems, Inc., the U.S. assignee of the present invention, is inserted into the vessel and advances against the occlusion in order to grind it into small particles that are passed by the body.

In many instances, a physician will place a stent in the area of the treated occlusion. In the case of balloon angioplasty, stents operate to prevent the compressed occlusion from springing back to its former size. For vessels that have undergone an atherectomy procedure, the stent helps maintain an open passage or lumen through the vessel.

Regardless of the procedure used, a fair percentage of stents become re-occluded within a relatively short period of time. However, the material that occludes the stent is somewhat different from the occluding material that blocked the vessel in the first instance. Therefore, techniques used to treat an original occlusion are not believed to be as effective when treating a re-occluded stent. Therefore, there is a need for a device and method of effectively treating re-occluded stents in a manner that does minimal or no damage to the stent itself.

SUMMARY OF THE INVENTION

The present invention is a system and method for removing occluding material from a stent that is positioned within a vessel. In one embodiment of the invention, a rotational cutter is made of a material having a hardness less than or equal to the hardness of the material used to make the stent. The cutter has a number of recessed blades such that the outer surface of the cutter is relatively smooth and cutting is limited to tissue that enters channels in which the blades are placed. The cutter is preferably routed on a guide wire that is shaped such that the cutter is pressed radially outward against the inner surface of the stent. To aid in the removal of ablated material that is cut from the stent, an aspiration system including a catheter coupled to a source of negative pressure operates to aspirate ablated particles.

In another embodiment of the invention, a cutting mechanism includes a catheter with a self-expanding stent on the distal end thereof. One or more knives are secured to the stent such that the knives are pushed radially outward by the stent. Once the expanding stent is positioned in an occluded stent, the one or more knives are extended and rotated to remove occluding material. Ablated material from the occluded stent is preferably aspirated from the vessel.

In another embodiment of the invention, a cutting mechanism includes a helically-wound cutter that surrounds an inflatable balloon. The balloon is inflated to urge the cutter radially outward against the inner wall of the stent. Ablated particles removed from the stent are preferably aspirated from the vessel.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 5A–5C illustrate various embodiments of helical cutters in accordance with other aspects of the present invention; and FIG. 6 illustrates a system for operating the helical cutter in accordance with another aspect of the present invention.

DETAILED DESCRIPTION OF THE PREFERRED EMBODIMENT

Figure 1:
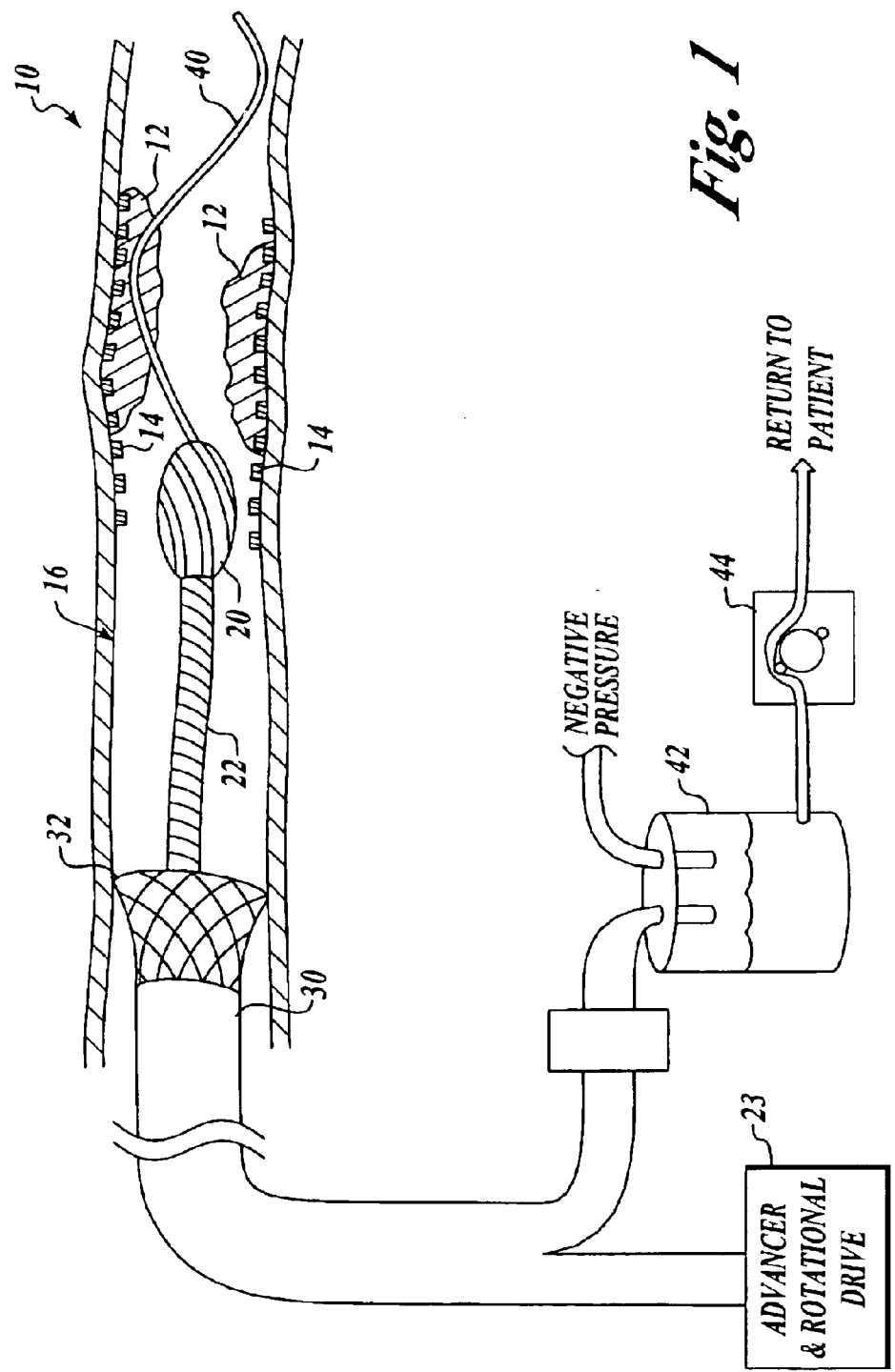
FIG. 1 shows a system for removing material from an occluded stent in accordance with one embodiment of the present invention.

FIG. 1 illustrates one embodiment of a system 10 for removing occluding matter 12 from a stent 14 that is positioned within a vessel 16 according to the present invention. As indicated above, the occluding material 12 is typically different from the occluding material generally associated with arteriosclerosis or other vascular diseases. Once the stent 14 is positioned in the vessel 12, the material 12 that re-occludes the stent is typically a smooth-celled growth that may continue to grow until the lumen or passage through the stent 14 is totally blocked.

To remove the occluding material 12 from the stent, the present invention includes a cutter 20 that is rotated by a drive shaft 22. The drive shaft 22 is advanced and rotated by an advancer/rotational drive 23 at the maximal end of the drive shaft 22. The cutter 20 and the drive shaft 22 are routed within a catheter 30 that is coupled to a source of negative pressure to provide a corresponding negative pressure or slight vacuum within the vessel 16 at the location of the stent. The catheter 30 may have a mechanism for sealing the catheter within the vessel such as a self-expanding stent 32 that is covered with an elastomeric coating such that when the stent 32 expands, the vessel is sealed. Alternatively, inflatable balloons at the end of the catheter 30 or other mechanisms may be used to seal the vessel in order to provide proper aspiration of the ablated particles.

To ensure that the cutter 20 clears a passage with a fairly large diameter, the cutter 20 is preferably routed over a guide wire 40 that is helical or otherwise shaped to force the cutter 20 toward the inner surface of the stent 14 when the cutter is advanced over the guide wire.

In some instances, it may be desirable to deliver a saline solution or other liquid through the drive shaft 22 and/or the cutter 20 to provide additional liquid volume in the vessel so that the vessel 16 doesn't collapse during aspiration. Saline and blood aspirated from the vessel are received in a collecting jar 42 and returned by a pump 44 to the patient via an intravenous drip or other mechanism.

Figure 3:
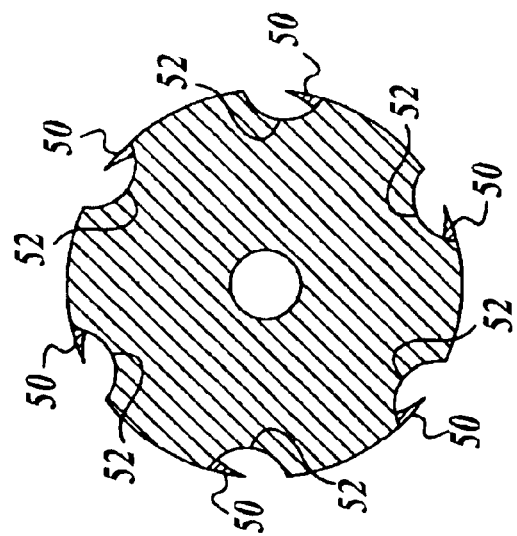
FIGS. 2 and 3 illustrate a cutter in accordance with another aspect of the present invention.
Figure 2:
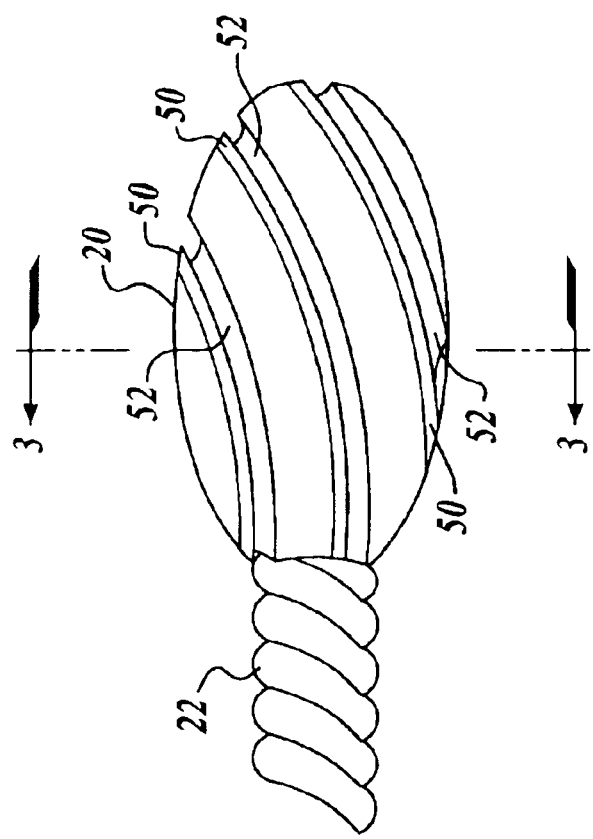

In order to prevent damage to the stent, the cutter 20 as shown in FIG. 2 is preferably made of a material that is soft or softer than the material from which the stent is made. Typically, the stent 14 is made is made of Nitinol™ or stainless steel. Therefore, the cutter 20 is preferably made of a material having a hardness less than or equal to Nitinol™ or stainless steel. As shown in FIG. 3, the cutter 20 has a number of recessed blades 50 that lie within corresponding channels 52. The blades 50 are positioned such that the outer surface of the cutter 20 is relatively smooth and will not catch or cut the inner surface of the stent 14. However, any occluding matter 12 that enters or is forced into the channels 52 is cut by the one or more blades 50 as the cutter 20 is rotated by the drive shaft 22. The channels 52 may be spiraled around the outer surface of the cutter 20 in order to force ablated material proximally as the burr is rotated in order to aid aspiration of the ablated tissue.

Figure 4:
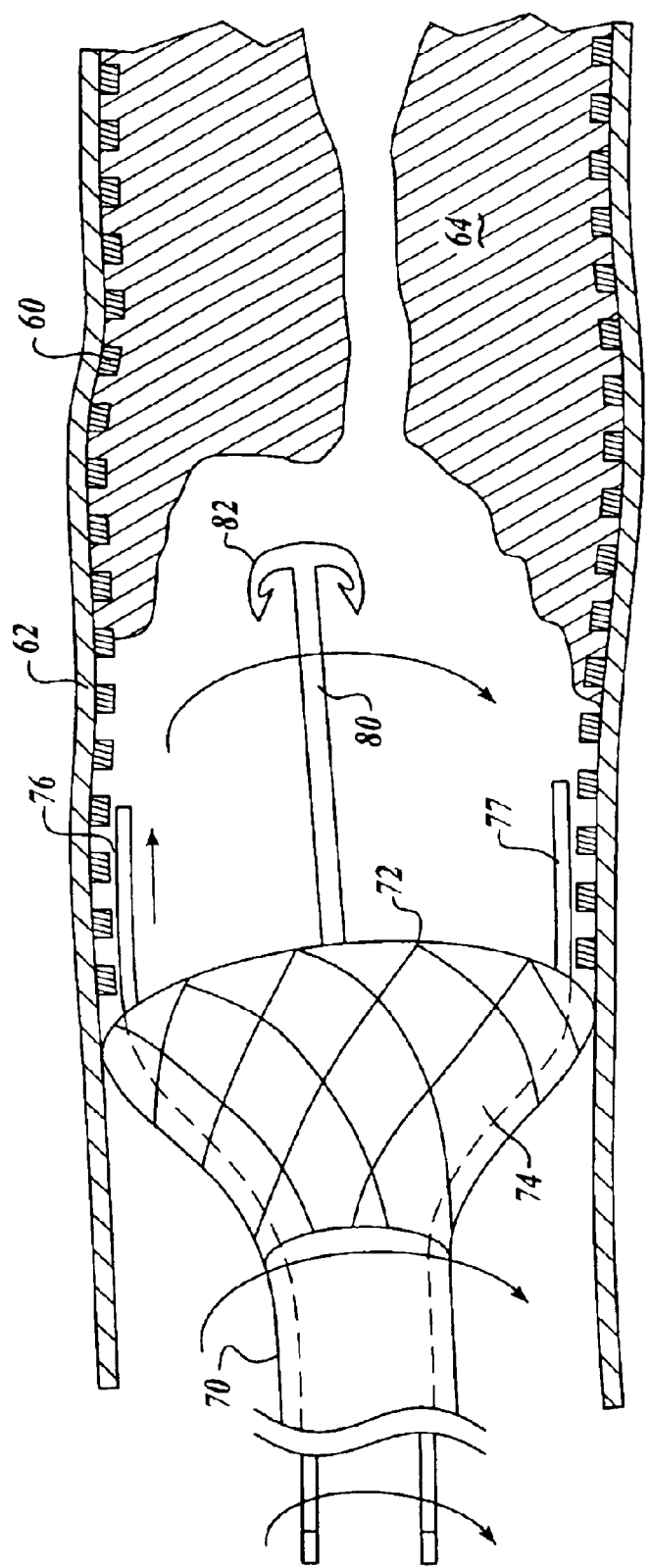
FIG. 4 illustrates a cutter for removing material from an occluded stent in accordance with yet another embodiment of the present invention.

FIG. 4 shows an alternative embodiment of a system for removing occluding matter from a stent. Here, a stent 60 is positioned within a vessel 62. The stent is shown as being fully blocked by occluding material 64. To remove the occluding material 64, a catheter 70 is inserted into the vessel. The catheter 70 has a self-expanding stent 72 at its distal end that is preferably covered with an elastomeric or other non-porous material 74 to seal the vessel when the stent 72 expands. One or more extendable cutting knives or blades 76, 77 are secured to the stent 72 such that when the stent is expanded, the one or more knives 76 are urged radially outward toward the vessel wall. In operation, the catheter 70 can be placed within or adjacent to the occluded stent 60. The self-expanding stent 72 is allowed to expand such that the one or more knives 76, 77 are positioned within the stent 60. Thereafter, the catheter 70, self-expanding stent 72, and one or more cutting knives 76, 77 are rotated within the stent to remove portions of the occluding matter 64. Aspiration can be applied to the catheter 70 to remove portions of the occluding material that are cut by the one or more cutting knives 76, 77.

To further hold the catheter 70 in position within the stent, a guide wire 80 has one or more hooks 82 (that may or may not be barbed) at its distal end that can be implanted into the occluding matter 64. The guide wire 80 serves an anchor against which the catheter 70 can be pulled in order to advance the one or more cutting knives 76, 77 within the occluded stent 60. Once the one or more cutting knives 76, 77 are rotated 360° in the stent 60, the guide wire 80 can be further advanced into the occluding material 64 and the process repeated.

Figure 5:
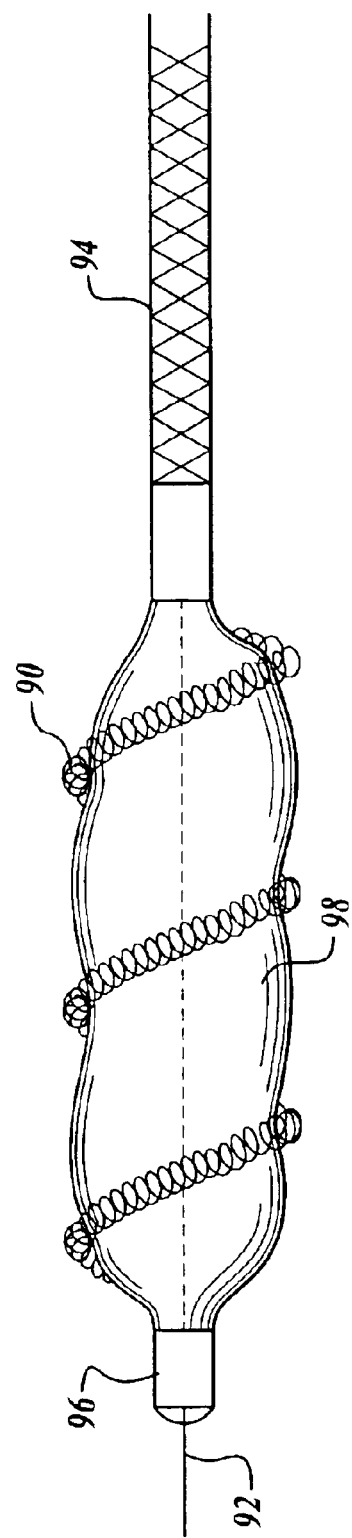
FIG. 5 illustrates a helical cutter in accordance with another aspect of the present invention.

FIG. 5 shows yet another alternative embodiment of a system for removing occluding matter from a stent in accordance with the present invention. In this embodiment, a helical cutter 90 extends around a guide wire 92 that is routed within a catheter 94. The cutter 90 extends from the end of the catheter 94 to a distal bearing 96 that is positioned on the guide wire 92. Within the helical cutter 90 is a balloon 98. The balloon 98 can be inflated with the saline or other material that is delivered through the catheter 94. Preferably, the catheter 94 is sealed along its length to prevent loss of the material used to inflate the balloon. Inflating the balloon 98 urges the helical cutter 90 radially outward toward the inner surface of a stent.

FIGS. 5A–5C show three of many possible embodiments of the helical cutter 90. The helical cutter 90 can comprise a generally round wire 100 that is selectively coated with an abrasive material such as diamond grit 102 as shown in FIG. 5A. The diamond grit is plated to a wire selectively such that the grit is not exposed on the surfaces that contact the stent itself, if the plated wire momentarily engages the stent, but only cuts deformable restenosis tissue that deforms in the abrasive.

Alternatively, as shown in FIG. 5B, the helical cutter 90 can comprise a relatively flat spring 104 having an outer edge 106 that is sharpened to provide a cutting surface. The material used to make the flat spring 104 preferably has a hardness that is less than or equal to the hardness of the material used to make the stent to be cleared.

Alternatively, as shown in FIG. 5C, the helical cutter 90 can comprise a cutaway tube, such as a hypotube, having a sharpened outer edge 110. The tube is wound into a helical coil around the guide wire. The material used to make the tube should have a hardness less or equal to the hardness of the material used to make the stent.

FIG. 6 shows how a helical cutter 90 of a type shown in FIG. 5 is used within a vessel. The helical cutter 90 is positioned within a partially or totally occluded stent 120 that is within a vessel 122. A catheter 130 is advanced into the vessel 122 and a sealing mechanism such as one or more balloons 134 at the distal end of the catheter is used to seal the vessel. A catheter 94 that contains the helical cutter 90 is then advanced through the catheter 94. The helical cutter 90 is expanded radially outward once it is within the stent 120 by inflating the balloon 98. The catheter 94 is then rotated by a prime mover such as gas turbine or an electric motor (not shown) at the proximal end of the catheters 94 and 130. Rotation of the helical cutter 90 removes the occluding material 124 from the stent 120. In addition, aspiration can be provided to the catheter 130 and/or 94 to remove portions of the ablated, occluding material 124. The aspirated material can be removed from the vessel using a pump 140 and a filter 144 before the aspirated liquid is returned to the patient.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for removing deposits from a partially or totally occluded stent, comprising:

a cutter that is insertable in the stent and when rotated removes deposits from the partially or totally occluded stent; and an expandable stent secured to the cutter, the expandable stent urging the cutter radially outward toward an inner wall of the stent when the expandable stent is expanded in a vessel;

wherein the expandable stent is covered with an elastomeric material.

2. A system for removing deposits from a partially or totally occluded stent, comprising:

a cutter having a hardness less than or equal to a hardness of the stent, the cutter having one or more recessed blades within one or more channels on the surface of the cutter to cut occluding matter that enters the channels; and a guide wire having a shape that directs the cutter radially outward toward an inner wall of the stent as the cutter is passed over it.

3. The system of claim 2, wherein the expandable stent forms a seal with the vessel when extended therein.

4. A system for removing deposits from a partially or totally occluded stent, comprising:

a catheter having an expandable stent at its distal end, the expandable stent having a distal end, wherein the expandable stent is covered with a non-porous material; and one or more cutting blades secured to the distal end of the expandable stent, the cutting blade having a hardness that is less than or equal to the hardness of the occluded stent;

wherein the expandable stent is expandable within the occluded stent such that the one or more cutting blades are urged toward an inner wall of the occluded stent and wherein the catheter and one or more cutting blades are rotatable to remove an occlusion from the occluded stent.

5. A method for removing restenotic tissue from within a stent, comprising:

advancing a cutter into the stent, the cutter including means for preventing damage to the stent;

rotating the cutter; and aspirating ablated particles of the restenotic tissue;

wherein the cutter is a rotating cutter and the means for preventing damage to the stent includes a number of recessed cutting blades.

* * * * *